United States Patent [19]

Lowry et al.

[11] Patent Number: 4,816,601

[45] Date of Patent: Mar. 28, 1989

[54] PROCESS FOR THE MANUFACTURE OF TRIMELLITIC ACID

[75] Inventors: James D. Lowry, Bolingbrook; Neal R. Nowicki, St. Charles; Walter Partenheimer, Naperville, all of Ill.

[73] Assignee: Amoco Corporation, Chicago, Ill.

[21] Appl. No.: 72,527

[22] Filed: Jul. 13, 1987

Related U.S. Application Data

[63] Continuation-in-part of Ser. No. 781,937, Sep. 30, 1985, abandoned, which is a continuation-in-part of Ser. No. 565,915, Dec. 27, 1983, abandoned.

[51] Int. Cl.[4] .......................................... C07C 51/265
[52] U.S. Cl. .................................................... 562/413
[58] Field of Search ....................................... 562/413

[56] References Cited

U.S. PATENT DOCUMENTS 3,683,016  8/1972  Darin et al. ......................... 562/413
3,920,735  11/1975  Wampfler et al. ................. 562/416

Primary Examiner—Michael L. Shippen
Attorney, Agent, or Firm—Gunar J. Blumberg; William H. Magidson; Ralph C. Medhurst

[57] ABSTRACT

A continuous process is disclosed for producing trimellitic acid by the liquid-phase air oxidation of pseudocumene in an acetic acid medium in the presence of a cobalt-manganese-bromine catalyst or a zirconium-cobalt-manganese-bromine catalyst wherein the mole ratio of cobalt-to-manganese is about 1.0:0,1 to about 1:5 and the ratio of zirconium-to-cobalt is about 0.005:1 to about 0.20:1, and mole ratio of bromine to total metals of said cobalt-manganese-bromine catalyst or zirconium-cobalt-manganese-bromine catalyst is from about 0.2:1.0 to about 2.0:1.0, which process comprises conducting the reaction continuously in two stages comprising a first-stage reaction at a temperature of about 250° F. to about 350° F. and a second-stage reaction at a temperature of about 350° F. to about 450° F. and recycling the cobalt-manganese catalyst or the zirconium-cobalt-manganese catalyst by oxalate precipitation of the catalyst at temperatures of about 250° F. to about 375° F. prior to the separation of mother liquor and using about 0.25 to about 2.5 moles of oxalic acid per mole of cobalt and manganese or mole of zirconium-cobalt-manganese and continuously recycling the recovered catalyst metals to the first-stage oxidation. The product of this novel process, trimellitic acid, is useful for the manufacture of polyamide-imides which are used as fibers or molded articles, including automotive parts.

12 Claims, 2 Drawing Sheets

FIG. 1

FIG. 2

CATALYST AND TRIMELLITIC ACID RECOVERY AS A FUNCTION OF SEPARATION TEMPERATURE

PROCESS FOR THE MANUFACTURE OF TRIMELLITIC ACID

CROSS-REFERENCES TO RELATED APPLICATIONS

This is a continuation-in-part application of Ser. No. 781,937, filed Sept. 30, 1985 which is a continuation-in-part of Ser. No. 565,915 filed on Dec. 27, 1983, now abandoned.

BACKGROUND OF THE INVENTION

The field of this invention relates to the liquid-phase continuous oxidation of pseudocumene to trimellitic acid.

The possibility of using liquid-phase instead of vapor-phase oxidation for the preparation of benzene carboxylic acids was first indicated by the disclosure in U.S. Pat. No. 2,245,528 of the catalysis provided by transition or variable-valence metals, especially cobalt, in temperatures from 100° C. to 320° C. and pressures to maintain the liquid phase of the aliphatic acid. Such catalysis, according to said patent, was advantageously promoted by the use of a ketone, such as methylethyl ketone, or aldehyde, such as acetaldehyde. It has been very difficult to manufacture trimellitic acid from pseudocumene in a continuous process because trimellitic acid (TMLA) is a catalyst deactivator. The usual process is to manufacture trimellitic anhydride from pseudocumene using a batch process. At start-up in a batch process, the concentration of TMLA is zero. As the process continues, concentration of TMLA builds up and deactivates the catalyst at the end of the process. In such prior art processes, the yields often do not exceed eighty-six mole percent and approximately two mole percent of high molecular weight impurities are formed.

It has been discovered that by employing a continuous process for the manufacture of trimellitic acid from pseudocumene, the yields of trimellitic acid are improved to 92 mole percent and the high molecular weight impurities are usually reduced about fifty percent to about one mole percent.

According to U.S. Pat. No. 3,920,735, the Mn-Br and Co-Mn-Br catalyst systems described in U.S. Pat. No. 2,245,528 are improved by the addition of zirconium. However, not mentioned, but illustrated in Tables I, II, and IV in U.S. Pat. No. 3,920,735 is the fact that, when part of the zirconium is added, combustion of the feedstock to carbon dioxide increases.

In the prior art, it has been known to use a staged catalyst addition oxidation of pseudocumene to prepare trimellitic anhydride in a batch method. For example, U.S. Pat. No. 3,683,016 to Darin, et al, teaches a method of staged catalyst addition of the catalyst components of cobalt, cerium and manganese in combination with a source of bromine wherein 10 to 25 percent of the manganese is added initially to the reaction in a first stage together with all the cobalt and approximately one-half of the cerium. The remaining 75 to 90 percent of the manganese together with cerium in an amount substantially equal to the cerium added in the first stage is added to the second stage. The reaction temperature of the first stage is in the range of 360° F. to 390° F. The temperature in the second stage is upward from 400° F., preferably from 400° F. to 435° F. The continuous method taught by Darin requires a series of batch operations wherein each staged addition of catalyst components is added to an oxidation vessel connected in series with the preceding vessel. The semi-continuous method of Darin also requires batch operation by batch addition of catalyst components. Accordingly, Darin, et al, U.S. Pat. No. 3,683,016 teaches batch methods to obtain continuous operation of staged catalyst addition using a cerium component catalyst at high temperatures to oxidize pseudocumene to trimellitic acid. However, in the instant invented continuous process, the oxidation mode is staged wherein pseudocumene is added continuously to the first oxidation stage, catalyst is added continuously during both oxidation stages, a cobalt-manganese-bromine catalyst or zirconium, cobalt-manganese-bromine catalyst is used, temperature of the first stage is from about 250° F. to about 350° F., temperature in the second stage is from about 350° F. to 450° F. and catalyst is continuously recycled as the oxalate salt to the first oxidation stage.

Also, U.S. Pat. No. 4,398,040, to Kitahara, et al, teaches a method of producing trimellitic acid by liquid-phase air oxidation of pseudocumene in acetic acid in the presence of cobalt, manganese and bromine as catalysts using a very low oxygen partial pressure whereby the reaction is in plural stages, the first stage at a temperature of 110° C. to 170° C. and the second stage at 180° C. to 240° C. In the examples, pressure in the first stage is 3.4 to 3.9 atm. and in the second stage, pressure is 22.3 atm. Reaction temperature is controlled by adjusting reaction pressure. Catalyst required by both stages of the oxidation process is taught as added in the first stage, and preferably not changed, by addition, to change the composition of the catalyst between the first stage of oxidation and the second stage of oxidation. Accordingly, Kitahara, et al, U.S. Pat. No. 4,398,040, teaches a method of staged temperature control by adjusting reaction pressure wherein catalyst addition is preferably not changed by further addition of catalyst after the first stage of oxidation. Catalyst recovery is by dehydrating the mother liquor. However, in the instant invented continuous process, there is taught a continuous method of staged oxidation wherein catalyst is added during both oxidation stages, and recycled, and the oxidation reaction stages are at low pressures. Reaction pressure is not a critical process variable. Additionally, catalyst recovery and recycle is by formation of oxalate salts.

SUMMARY OF THE INVENTION

A continuous process is disclosed for producing trimellitic acid by the liquid-phase air oxidation of pseudocumene in a mother liquor comprising an acetic acid medium in the presence of a cobalt-manganese-bromine catalyst or a zirconium-cobalt-manganese-bromine catalyst wherein the mole ratio of cobalt-to-manganese is about 1:0.2 to about 1:1 and the mole ratio of zirconium-to-cobalt in the catalyst is about 0.01:1 to about 0.1:1, and mole ratio of bromine to total metals of said cobalt-manganese-bromine catalyst or said zirconium-cobalt-manganese-bromine catalyst is from about 0.2:1.0 to about 2.0:1.0, which process comprises conducting the reaction in two stages comprising a first-stage reaction at a temperature of about 250° F. to about 350° F. and a second-stage reaction at a temperature of about 350° F. to about 450° F. and recycling the cobalt-manganese catalyst or the zirconium-cobalt-manganese catalyst by oxalate precipitation of the catalyst at temperatures of about 250° F. to about 375° F. prior to the separation of mother liquor and using about 0.25 moles to about 2.5 moles of oxalic acid per total moles of cobalt and manganese or total moles of zirconium-cobalt-manganese and continuously recycling the recovered catalyst metals to the first-stage oxidation. The product of this novel process, trimellitic acid, is useful for the manufacture of polyamide-imides which are used as fibers or molded articles, including automotive parts.

DETAILS OF THE INVENTION

Our novel process relates to the liquid-phase air oxidation of pseudocumene to trimellitic acid in a mother liquor comprising an acetic acid medium wherein weight ratio of pseudocumene to acetic acid is in the range of from about 1:1 to about 1:5 using cobalt, manganese, and/or other variable-valence metals, such as zirconium, plus bromine. Our novel invention is a process for the oxidation of trimethylbenzenes with molecular oxygen to benzene tricarboxylic acid under liquid-phase conditions in the presence of a cobalt-manganese-bromine catalyst or a zirconium-cobalt-manganese-bromine catalyst wherein the mole ratio of zirconium to cobalt is 0.0 to about 0.1. The process comprises conducting a oxidation of pseudocumene in a two-stage oxidation wherein the first stage is conducted continuously at a relatively low temperature of about 250° F. to about 350° F. followed by a second continuous oxidation at a more severe temperature of about 350° F. to about 450° F. In this continuous process, additional catalyst is fed during the second stage to avoid the deactivation of the catalyst. It is critical to the continuous process that catalyst be added at the second stage continuously since the trimellitic acid product and other polycarboxylic acids deactivate the catalyst.

Our process is a continuous process for producing trimellitic acid by the liquid-phase air oxidation of pseudocumene in a mother liquor comprising an acetic acid medium in the presence of a cobalt-manganese-bromine catalyst wherein the mole ratio of cobalt to manganese is from about 1.0:0.1 to about 1.0:5.0, preferably from about 1.0:0.2 to about 1.0:1.0, which process comprises conducting the reaction in two stages comprising a first-stage reaction at a temperature of about 250° F. to about 350° F. and a second-stage reaction at a temperature of about 350° F. to about 450° F. and recycling the cobalt-manganese catalyst by oxalate precipitation of the catalyst at temperatures of about 250° F. to about 375° F. prior to the separation of mother liquor and using about 0.25 to about 2.5 moles of oxalic acid per total moles of cobalt and manganese in the first oxidation stage and recycling the cobalt and manganese oxalates to the first-stage oxidation. Preferably, the mole ratio of the oxalic acid to the cobalt-manganese catalyst is about 0.5 to about 1.5. Mole ratio of bromine to total metals of the cobalt-manganese-bromine catalyst is from about 0.2:1.0 to about 2.0:1.0, preferably from about 0.5:1.0 to 1.5:1.0, bromine moles to total metal moles.

The present invention is a continuous process for producing trimellitic acid by the liquid-phase air oxidation of pseudocumene in a mother liquor comprising an acetic acid medium in the presence of a zirconium-cobalt-manganese-bromine catalyst wherein the mole ratio of zirconium-to-cobalt in the catalyst is from about 0.005:1 to about 0.2:1, preferably from about 0.01:1 to about 0.1:1, which process comprises conducting the reaction at two stages comprising a first-stage reaction at a temperature of about 250° F. to about 350° F. and a second-stage reaction at a temperature of about 350° F. to about 450° F. and recycling the zirconium-cobalt-manganese catalyst by oxalate precipitation of the catalyst at temperatures of about 250° F. to about 375° F. prior to the separation of mother liquor and using about 0.25 to about 2.5 moles of oxalic acid per total moles of zirconium, cobalt, and manganese and continuously recycling the zirconium-cobalt-manganese oxlates to the first-stage oxidation. Preferably, the mole ratio of oxalic acid to zirconium-cobalt-manganese catalyst is about 0.5 to about 1.5. Mole ratio of bromine to total metals of the zirconium-cobalt-manganese-bromine catalyst is from about 0.2:1.0 to about 2.0:1.0, preferably from about 0.5:1 to about 1.5:1, bromine moles to total metal moles.

Since catalyst has to be added in the second stage for the mode of operation, the catalyst has to be recovered and recycled. This recycle process is difficult since the catalyst metals coprecipitate with the trimellitic acid product during crystallization. To overcome this difficulty, our novel process includes a novel catalyst recovery process which comprises a high temperature of about 250° F. to about 375° F. and an oxalate precipitation in a separate step. According to our recovery process, cobalt recoveries in excess of 95% have been obtained as shown in Table 2. Cobalt is the most expensive component of the catalyst.

In our recovery process, the oxalate precipitation is preferred right after the second-stage oxidation at temperatures of about 250° F. to about 375° F., prior to the separation of the mother liquor. In our recovery process, only small amounts of oxalic acid are required, usually about a 1:1 mole ratio; with the catalyst metals; however, we can use mole ratios of oxalic acid to total cobalt and manganese of about 0.25:1 to about 2.5:1. In our recovery process, the oxalate salts form rapidly, even from cobalt and manganese, or cobalt, manganese and zirconium, previously tied up as insoluble trimellitate salts. The oxalates are readily recovered from the acetic acid solvent, in which they are insoluble, by high temperature separation, by, for example, high pressure centrifugation, or by hydroclones.

It is particularly advantageous to run the precipitation step at a temperature of about 275° F. to about 325° F. so that a very high percentage, in excess of about 70 percent, of the product trimellitic acid remains dissolved in the mother liquor and is readily separated from the catalyst precipitate. Temperatures in excess of about 375° F. cannot be used in our recovery process, since the oxalate salts of cobalt, manganese and zirconium decompose. The thermal instability of the oxalate salts enables us to directly recycle these compounds to the pseudocumene oxidation reactors. Under our process oxidation conditions of about 250° F. to about 450° F., the oxalate salts regenerate to the active catalyst metals.

A batch oxidation was initiated by charging a 2:1 mole ratio of pseudocumene (PSC) and first-stage catalyst solution. After externally heating the reactor contents to about 350° F., a compressed oxygen/nitrogen stream was introduced. When the temperature was sustained without external heat, fresh reactant feeds were started. PSC and catalyst solutions were independently heated and fe to the reactor. When the operating level was reached, first-state product was transferred to a slop receiver. After two to three residence times, first-stage product was diverted to the second-stage reactor. A compressed oxygen/nitrogen stream and additional preheated catalyst solution were also introduced to this reactor. Product was continuously transferred to a slop vessel for three to five residence times, then was diverted into a sample receiver. Once a sufficient sample was collected (8 to 10 lbs), the reaction was terminated.

After depressuring the vessels, the first- and second-stage reactors and second-stage samples were drained, weighed, and samples retained for analysis. Caustic washes were also performed on each vessel, and each vessel was drained, weighed, and samples were retained for analysis.

Rates of liquid stream addition were monitored by electronic scales while air feeds were measured with orifice plates and DP meters. The reactor liquid level was controlled with a combination of a radioactive-type detector and an on/off timed transfer valve. Several liquid and gas temperatures were monitored throughout the system. The concentration of carbon dioxide and carbon monoxide in the reactor's off-gas were measured with infrared detectors (Beckmann Series 864), while the oxygen concentration was monitored with an osmotic pressure-type detector (Beckmann Series 7003).

Pseudocumene used was that utilized by commercial facilities manufacturing trimellitic acid. Glacial acetic acid and cobalt and manganese acetate tetrahydrates were purchased from Chemical Exchange Corp. and were all reagent grade. The bromide source was an aqueous solution of 48% hydrobromic acid, purchased from Great Lakes Corp. A 17.5% solution of aqueous zirconium acetate was also used. All water was distilled and deionized.

Slurry samples from the first-stage reactor and second-stage sample vessel were analyzed by gradient liquid chromatography (LC) for trimellitic acid (TMLA), methyl dibasic acids (MDB), dimethyl benzoic acids (DMB), PSC, benzoic acid (BA), toluic acid, hemimellitic acid (HLA), and trimesic acid (TRA). Slurry samples were also analyzed for high boilers by esterification gas chromatography, total aldehydes by a standard polarographic technique and total solids by drying in a vacuum oven at 100° F. Catalyst feeds and slurry samples were analyzed for water by Karl Fisher titration and for cobalt, manganese, and bromine by using a Kevex X-ray fluorescence spectrophotometer. Slurry samples were dissolved in 10% ammonium hydroxide to free catalyst precipitated with product.

Caustic wash samples from all three vessels were analyzed for TMLA and methyl dibasic acids by gradient LC. A total estimate of solids in the sample was then made by ratioing the sum of TMLA and methyl dibasics to the total solids in the vessel drain to the sum of the TMLA and methyl dibasics in caustic sample. The concentration of acetic acid was also measured in the caustic sample by a gas chromatography method in order to estimate the retained solvent. This information was used in residence time calculations.

In summary, the instant invention comprises a continuous process for producing trimellitic acid by the continuous liquid-phase air oxidation of pseudocumene in a mother liquor comprising an acetic acid medium to trimellitic acid wherein weight ratio of pseudocumene to acetic acid is in the range of from about 1:1 to about 1:5, preferably from about 1:1.5 to about 1:3, air oxygen partial pressure is in the range of from about 1 psi to about 20 psi, preferably from about 3.0 psi to about 10.0 psi in the presence of a cobalt-manganese-bromine catalyst wherein the mole ratio of cobalt-to-manganese is from about 1.0:0.1 to about 1.0:5.0, preferably from about 1:0.2 to about 1:1, the process comprising oxidation of pseudocumene in two stages comprising a first-stage oxidation at a temperature of about 250° F. to about 350° F. and a secondstage oxidation at a temperature of about 350° F. to about 450° F. wherein both air and the cobalt-manganese-bromine catalyst are added during both oxidation stages and recycling the cobalt-manganese metals of said catalyst by oxalate precipitation of metals of said catalyst at temperatures of about 250° F. to about 375° F. prior to the separation of said mother liquor from said trimellitic acid and using about 0.25 to about 2.5 moles of oxalic acid for the total moles of cobalt and manganese metals of said catalyst and continuously recycling the cobalt and manganese oxalates to the first-stage oxidation wherein mole ratios of said oxalic acid to said cobalt-manganese catalyst is preferably about 0.5:1 to about 1.5:1, and mole ratio of bromine to total metals of the cobalt-manganese-bromine catalyst is from about 0.2:1.0 to about 2.0:1.0, preferably from about 0.5:1 to about 1.5:1, bromine moles to total metals moles.

The instant invention also comprises a continuous process for producing trimellitic acid by the continuous liquid-phase air oxidation of pseudocumene in a mother liquor comprising an acetic acid medium to trimellitic acid wherein weight ratio of pseudocumene to acetic acid is in the range of from about 1:1 to about 1:5, preferably from about 1:1.5 to about 1:3, air oxygen partial pressure is in the range of from about 1 psi to about 20 psi, preferably from about 3.0 to about 10.0 psi in the presence of a zirconium-cobalt-manganese-bromine catalyst wherein the mole ratio of zirconium-to-cobalt in the catalyst is from about 0.005:1.0 to about 0.2:1.0, preferably about 0.01:1 to about 0.10:1, which process comprises conducting the oxidation of two stages comprising a first-stage reaction at a temperature of about 250° F. to about 350° F. and a second-stage oxidation at a temperature of about 350° F. to about 450° F. wherein both air and the zirconium-cobalt-manganese-bromine catalyst are added during both oxidation stages and recycling the zirconium-cobalt-manganese metals of said catalyst by oxalate precipitation of metals of said catalyst at temperatures of about 250° F. to about 375° F. prior to the separation of said mother liquor irom said trimellitic acid and using about 0.25 to about 2.5 moles of oxalic acid for the total moles of the zirconium, cobalt and manganese metals of said catalyst and continuously recycling the zirconium-cobalt-manganese oxalates to the first-stage oxidation. Preferably, mole ratio of said oxalic acid to said zirconium-cobalt-manganese catalyst is about 0.5:1 to about 1.5:1, and mole ratio of bromine to total metals of the zirconium-cobalt-manganese-bromine catalyst is from about 0.2:1.0 to about 2.0:1.0, preferably from about 0.5:1 to about 1.5:1, bromine moles to total metal moles.

The following examples illustrate the process of the instant invention but are not to be construed as limiting the scope of the invention.

EXAMPLE I

The following example illustrates the two-stage continuous oxidation of pseudocumene to trimellitic acid which is conducted as follows: The pilot unit was operated in continuous method with two continuous stages of oxidation. The primary reactor had a total volume of 0.6 ft$^3$, while the second-stage vessel contained a volume of 0.1 ft$^3$. Each vessel had an overhead knockback condenser for evaporative cooling, a pressure control system, an air-driven mixer, and baffles. The primary reactor also had capability to provide internal liquid-phase cooling using an oil-cooled coil. All materials of construction in the reactor system were titanium. The first-stage temperature was 267° F. while the second-stage temperature was maintained at 410° F.. The total catalyst usage was 0.87 weight percent on a pseudocumene basis, with equal amounts of the catalyst being added to each stage. The residence time of oxidation was 112 minutes with 80% of the hold time occurring in the first stage. The water was held near batch levels at 22 wt % to 24 wt % in the reactor solvent. The first-stage reactor solvent ratio was 1.6 with solvent addition to the second stage increasing the ratio to 2.7. The partial pressure of oxygen was maintained near 5 psi in each stage. These conditions resulted in an 87.1 mole% yield of trimellitic acid (TMLA) with 6.4 mole% partially reacted and recoverable intermediates.

Further details are in Table 1.

TABLE 1

Two-Stage Acetic Acid-Based Pseudocumene (PSC) Oxidation
7455-110

|  | 1st Stage | 2nd Stage |
|---|---|---|
| Process Conditions |  |  |
| Temperature (°F.) | 267 | 410 |
| Residence Time (min) | 88 | 24 |
| Co (wt % pseudocumene) | 0.47 | 0.87 |
| Mn/Co Mole Ratio | 0.32:1 | 0.30:1 |
| Zr/Co Mole Ratio | 0.011:1 | 0.010:1 |
| Br/Total Metals Mole Ratio | 1.4:1 | 1.4:1 |
| Water (wt % solvent) | 24 | 22 |
| Solvent Weight Ratio (reactor) | 1.6 | 2.7 |
| Oxygen Pressure (psi) | 4.8 | 5.5 |
| Results |  |  |
| $O_2$ Consumption (mole (m) $O_2$/mole (m) pseudocumene) | 3.6 | 0.9 |
| Product Distribution (mole %)[a] |  |  |
| Pseudocumene (PSC) |  | 0.1 |
| Aldehydes |  | 1.2 |
| Dimethyl Benzoic Acids (DMB) |  | 0.1 |
| Methyl Dibasic Acids (MDB) |  | 5.0 |
| Trimellitic Acid (TMLA) |  | 87.1 |
| Isophthalic Acid/Orthophthalic Acid/Terephthalic Acid |  | 1.3 |
| Benzoic Acid (BA) |  | 0.2 |
| Toluic Acid |  | 0.1 |
| Hemimellitic Acid (HMLA) |  | — |
| Trimesic Acid (TRA) |  | 0.1 |
| High Boilers (HB) |  | 0.9 |
| $CO_x$'s |  | 3.9 |
| Yield (lb TMLA/lb PSC) |  | 1.62 |
| Acetic Acid Consumption lb/lb TMLA |  | 0.039 |

[a]The trimellitic acid yields quoted in the text include methyl dibasic acid (MDB) intermediates which would oxidize to TMLA product upon recycle to the oxidation reactor.

EXAMPLE II

The following example illustrates the catalyst recovery process. 439 grams of pilot plant slurry were charged into a one-liter titanium-clad autoclave reactor. The reactor was heated to 300° F. under nitrogen and maintained for approximately 10 minutes. Oxalic acid at a 1.22 mole ratio was added as a dilute aqueous solution using a Ruska pump. After approximately 5 minutes, a valve at the bottom of the reactor was opened to start the filtration. Some plugging of the one-micron titanium filter was observed; however, the plug was removed by increasing the reactor pressure. Filtration was completed in approximately 10 minutes.

Table 2 summarizes the results of the pilot plant run. As can be seen from this data, greater than 98% of the cobalt and 47% of the manganese were recovered by this procedure. By adding the oxalic acid as a dilute solution, the solvent ratio has been significantly increased from 3.2:1 to 3.9:1. The result was that nearly all of the TMLA was soluble at the 300° F. separation temperature. Out of 439 grams of slurry (31.0 by weight solids) only 3.64 grams of solids were recovered on the filter. The oxalate salts of cobalt and manganese recovered can account for 68% of this weight. The remainder was believed to be trimellitic acid.

TABLE 2

Catalyst Recovery in Trimellitic Acid Slurry by Oxalate Precipitation at 305° F.[a]

| Starting Material (g) |  |  |
|---|---|---|
| Sample Weight |  | 439.0 |
| Solids |  | 136.0 |
| % Total Solids (TS) |  | 31.0 |
| Catalyst |  |  |
| Co |  | 0.714 |
| Mn |  | 0.162 |
| Br |  | 1.707 |
| Oxalic Acid |  | 2.3[b] |
| Run Number |  | 6090-184 |
| Sample (g) | Precipitate | Filtrate |
| Sample Weight | 3.64 | 502.0 |
| Dried Solids | — | 109.9 |
| % Total Solids (TS) | — | 21.9% |
| Catalyst |  |  |
| Co | 0.728 | 0.012 |
| Mn | 0.069 | 0.076 |
| Br | 0.006 | 1.518 |
| Catalyst Recovery (%) |  |  |
| Co | 98.4 |  |
| Mn | 47.6 |  |
| Accountability | Wt (g) | % Accountability |
| Total Sample | 505.6 | 95.8 |
| Solids | 111.2 | 81.8 |
| Catalyst: |  |  |
| Co | 0.740 | 103.6 |
| Mn | 0.145 | 89.5 |
| Br | 1.524 | 89.3 |

[a]Runs were made using continuous feed material in a one-liter titanium-clad autoclave.
[b]Oxalic acid dihydrate was added as a 2.6% by weight aqueous solution.

EXAMPLES III-V

In the invented two-stage acetic acid solvent-pseudocumene oxidation process, the two most critical process variables are catalyst and temperature. A series of runs were conducted to illustrate the effects of reaction temperature on catalyst usage, oxidation yield, and acetic acid consumption. The reaction temperature was varied maintaining, however, a constant level of intermediates in the oxidation effluent. The process conditions and analytical results for the runs are reported in Table 3 wherein the effects of changing catalyst and temperature are shown.

As the data in Table 3 show, the first-stage temperatures were varied from about 270° F. to about 320° F. and the second-stage temperatures were changed proportionally from about 420° F. to about 450° F. The concentration of the catalyst metals was reduced from about 0.8 to about 0.13 weight percent of the pseudocumene feed as temperatures increased in an attempt to obtain similar rates of reaction and resulting conversion to product. As progressively higher temperatures were used, the manganese-to-cobalt ratio was increased and less catalyst was added to the second stage. The catalyst was exchanged in this manner in order to further minimize catalyst costs (manganese is a less expensive catalyst component). Other process conditions were held constant. Total residence times were held at 160 minutes with 75% of the hold time in the first stage. The reactor water concentrations were about 24 to about 27 percent. Additional solvent was added to the second stage, thereby increasing the solvent-to-hydrocarbon weight ratio of about 1.6 in the first stage to about 2.8 in the second stage. Partial pressures of oxygen were maintained between about 5 to about 9 psi and bromine-to-metals ratios were held at about 1.2 to about 1.3. In our novel process, we determined that higher partial pressures of oxygen reduce the formation of high molecular weight by-products and, as such, improve product yields and quality. The higher levels of bromine were used to help prevent catalyst deactivation.

Table 3 illustrates that as temperature is increased, it is possible to reduce catalyst loading, but yield goes down and acetic acid consumption increases. Yields in excess of 91 mole% were obtained at the lower temperatures tested; however, the yield drops off to less than 83 mole% at the higher temperatures. Paralleling the yield decreases, $CO_x$ formation, high boilers, terephthalic acid/isophthalic acid/phthalic acid (TA/IA/OA) and benzoic acid all significantly increase at the high temperatures. Similarly, optical product quality is degraded at the higher temperatures. Losses to burning were directly proportional to temperature, increasing from about 1.4 to about 2.2 times batch levels. Thus, the preferred temperature for the operation of our process is at about 250° F. to about 280° F. in the first stage and about 400° F. to about 425° F. in the second stage at a 0.8 weight percent cobalt-on-pseudocumene feed.

TABLE 3

Effects of Exchanging Catalyst and Temperature in Two-Stage Acetic Acid-Based Pseudocumene Oxidation to Trimellitic Acid

|  | Example III 7455-145 | | Example IV 7455-130 | | Example V 7455-145 | |
|---|---|---|---|---|---|---|
|  | 1st | 2nd | 1st | 2nd | 1st | 2nd |
| Process Conditions | | | | | | |
| Temperature (°F.) | 271 | 420 | 296 | 434 | 321 | 447 |
| Residence Time (min) | 121 | 34 | 120 | 41 | 120 | 33 |
| Co (wt % PSC) | 0.45 | 0.80 | 0.28 | 0.36 | 0.13 | 0.15 |
| Mn/Co Mole Ratio | 0.30:1 | 0.29:1 | 0.53:1 | 0.56:1 | 0.89:1 | 1.0:1 |
| Zr/Co Mole Ratio | 0.013:1 | 0.011:1 | 0.012:1 | 0.012:1 | 0.017:1 | 0.016:1 |
| Br/Total Metals Mole Ratio | 1.3:1 | 1.2:1 | 1.2:1 | 1.2:1 | 1.3:1 | 1.2:1 |
| Water (wt % solvent) | 27 | 24 | 26 | 24 | 24 | 23 |
| Solvent Weight Ratio (reactor) | 1.6 | 2.8 | 1.6 | 2.7 | 1.7 | 2.9 |
| Oxygen Pressure (psi) | 6.5 | 8.8 | 8.1 | 5.1 | 8.8 | 6.1 |
| Results | | | | | | |
| $O_2$ Consumption (m $O_2$/m PSC) | 4.1 | 1.0 | 4.1 | 1.6 | 4.0 | 1.4 |
| Product Distribution (mole %) | | | | | | |
| PSC |  | 0.1 |  | 0.1 |  | 0.1 |
| Aldehydes |  | 0.5 |  | 0.6 |  | 3.0 |
| DMB |  | 0.1 |  | 0.1 |  | 0.8 |
| MDB |  | 1.2 |  | 1.5 |  | 11.3 |
| TMLA |  | 89.5 |  | 84.5 |  | 70.0 |
| IA/OA/TA |  | 1.0 |  | 2.0 |  | 2.2 |
| BA |  | 0.1 |  | 0.2 |  | 0.4 |
| Toluic Acid |  | 0.1 |  | 0.1 |  | 0.1 |
| HMLA |  | — |  | — |  | — |
| TRA |  | 0.1 |  | 0.1 |  | 0.1 |
| HB |  | 1.1 |  | 1.4 |  | 1.8 |
| $CO_x$'s |  | 6.3 |  | 9.4 |  | 10.1 |
| Yield (lb TMLA/lb PSC) |  |  |  |  |  | 1.452 |
| Acetic Acid Consumption (lb/lb TMLA) |  |  |  |  |  | 0.113 |

EXAMPLE VI

The independent effect of reactor temperature on our novel two-stage process is illustrated in this example and in Table 4. Both first- and second-stage temperatures were proportionally changed. Most of the other process conditions were held relatively constant except for the residence time. In the low temperature experiment (Run No. 7455-095), the total residence time was about 10% longer than the high temperature experiment (Run No. 7455-085). Advantageously, the lowering of the first-stage reaction temperature from about 312° F. to about 287° F. resulted in decreased losses to carbon oxides and high boilers but surprisingly, no change in the level of intermediates was measured. Surprisingly, the net result was an increase in yield and decrease in acetic acid consumption at the lower temperature. The data are set forth in Table 4.

TABLE 4

Effects of Temperature in Acetic Acid-Based Pseudocumene Oxidation to Trimellitic Acid

|  | 7455-085 | | 7455-095 | |
|---|---|---|---|---|
|  | 1st | 2nd | 1st | 2nd |
| Process Conditions | | | | |
| Temperature (°F.) | 312 | 438 | 287 | 427 |
| Residence Time (min) | 64 | 25 | 78 | 23 |
| Co (wt % PSC) | 0.51 | 0.84 | 0.47 | 0.87 |
| Mn/Co Mole Ratio | 0.29:1 | 0.30:1 | 0.28:1 | 0.27:1 |

TABLE 4-continued

Effects of Temperature in Acetic Acid-Based
Pseudocumene Oxidation to Trimellitic Acid

| | 7455-085 | | 7455-095 | |
|---|---|---|---|---|
| | 1st | 2nd | 1st | 2nd |
| Zr/Co Mole Ratio | 0.047:1 | 0.047:1 | 0.049:1 | 0.048:1 |
| Br/Total Metals Mole Ratio | 1.3:1 | 1.3:1 | 1.4:1 | 1.4:1 |
| Water (wt % solvent) | 31 | 26 | 30 | 23 |
| Solvent Weight Ratio (reactor) | 1.7 | 2.7 | 1.7 | 2.8 |
| Oxygen Pressure (psi) | 5.0 | 9.0 | 6.0 | 7.7 |
| Results | | | | |
| $O_2$ Consumption (m $O_2$/m PSC) | 4.3 | 1.1 | 4.2 | 0.7 |
| Product Distribution (mole %) | | | | |
| PSC | | 0.1 | | 0.1 |
| Aldehydes | | 0.9 | | 0.8 |
| DMB | | 0.1 | | 0.1 |
| MDB | | 1.8 | | 1.8 |
| TMLA | | 82.3 | | 86.9 |
| IA/OA/TA | | 1.0 | | 1.3 |
| BA | | 0.3 | | 0.3 |
| Toluic Acid | | 0.3 | | 0.1 |
| HMLA | | — | | — |
| TRA | | 0.4 | | 0.1 |
| HB | | 1.8 | | 1.1 |
| $CO_x$'s | | 11.0 | | 7.4 |
| Yield (lb TMLA/lb PSC) | | 1.48 | | 1.56 |
| Acetic Acid Consumption (lb/lb TMLA) | | 0.120 | | 0.077 |

EXAMPLE VII

The effects of partial pressure of oxygen on the oxidation were tested. Results are in Table 5. Again, all other process conditions were held constant except for the residence time. In the high partial pressure experiment (Run No. 7455-145), the total residence time was approximately 10% longer. The results indicate that about a 1.5-fold increase in the partial pressure of oxygen in the first stage and about a 2.6-fold increase in the second stage resulted in a significant improvement in yield. The yield of trimellitic acid was improved from about 86 to about 90 mole percent. The yield increase resulted primarily from a 50% decrease in intermediates, but there was also a 10% decrease in losses to carbon oxides.

TABLE 5

Effects of Partial Pressure of Oxygen in Acetic
Acid-Based Pseudocumene Oxidation to Trimellitic Acid

| | 7455-140 | | 7455-145 | |
|---|---|---|---|---|
| | 1st | 2nd | 1st | 2nd |
| Process Conditions | | | | |
| Temperature (°F.) | 271 | 423 | 271 | 420 |
| Residence Time (min) | 106 | 32 | 121 | 34 |
| Co (wt % PSC) | 0.47 | 0.82 | 0.45 | 0.80 |
| Mn/Co Mole Ratio | 0.29:1 | 0.27:1 | 0.30:1 | 0.29:1 |
| Zr/Co Mole Ratio | 0.012:1 | 0.011:1 | 0.013:1 | 0.011:1 |
| Br/Total Metals Mole Ratio | 1.3:1 | 1.4:1 | 1.3:1 | 1.2:1 |
| Water (wt % solvent) | 28 | 24 | 27 | 24 |
| Solvent Weight Ratio (reactor) | 1.7 | 2.8 | 1.6 | 2.8 |
| Oxygen Pressure (psi) | 4.3 | 3.4 | 6.5 | 8.8 |
| Results | | | | |
| $O_2$ Consumption (m $O_2$/m PSC) | 4.0 | 1.3 | 4.1 | 1.0 |
| Product Distribution (mole %) | | | | |
| PSC | | 0.1 | | 0.1 |
| Aldehydes | | 1.0 | | 0.5 |
| DMB | | 0.2 | | 0.1 |
| MDB | | 2.7 | | 1.2 |
| TMLA | | 86.0 | | 89.5 |
| IA/OA/TA | | 1.1 | | 1.0 |
| BA | | 0.7 | | 0.1 |
| Toluic Acid | | 0.1 | | 0.1 |
| HMLA | | — | | — |
| TRA | | 0.1 | | 0.1 |
| HB | | 1.1 | | 1.1 |
| $CO_x$'s | | 7.0 | | 6.3 |
| Yield (lb TMLA/lb PSC) | | 1.56 | | 1.59 |
| Acetic Acid Consumption (lb/lb TMLA) | | 0.073 | | 0.064 |

EXAMPLE VIII

The effect of the zirconium/cobalt ratio on the oxidation was tested. Results are in Table 6. In this run, all other process conditions were held constant. The results indicate that a 3-fold increase in zirconium resulted in a 2.6-fold decrease in intermediates and a 15% decrease in by-products.

TABLE 6
Effects of Zr/Co Ratio in Acetic Acid-Based Pseudocumene Oxidation to Trimellitic Acid

|  | 7455-095 | | 7455-100 | |
| --- | --- | --- | --- | --- |
|  | 1st | 2nd | 1st | 2nd |
| Process Conditions | | | | |
| Temperature (°F.) | 287 | 427 | 287 | 429 |
| Residence Time (min) | 78 | 23 | 80 | 22 |
| Co (wt % PSC) | 0.47 | 0.87 | 0.48 | 0.83 |
| Mn/Co Mole Ratio | 0.28:1 | 0.27:1 | 0.29:1 | 0.27:1 |
| Zr/Co Mole Ratio | 0.049:1 | 0.048:1 | 0.017:1 | 0.016:1 |
| Br/Total Metals Mole Ratio | 1.4:1 | 1.4:1 | 1.3:1 | 1.4:1 |
| Water (wt % solvent) | 30 | 23 | 26 | 23 |
| Solvent Weight Ratio (reactor) | 1.7 | 2.8 | 1.6 | 2.7 |
| Oxygen Pressure (psi) | 6.0 | 7.7 | 5.8 | 6.2 |
| Results | | | | |
| $O_2$ Consumption (m $O_2$/m PSC) | 4.2 | 0.7 | 3.8 | 0.9 |
| Product Distribution (mole %) | | | | |
| PSC |  | 0.1 |  | 0.1 |
| Aldehydes |  | 0.8 |  | 1.6 |
| DMB |  | 0.1 |  | 0.2 |
| MDB |  | 1.8 |  | 5.3 |
| TMLA |  | 86.9 |  | 83.3 |
| IA/OA/TA |  | 1.3 |  | 1.4 |
| BA |  | 0.3 |  | 0.3 |
| Toluic Acid |  | 0.1 |  | 0.1 |
| HMLA |  | — |  | — |
| TRA |  | 0.1 |  | 0.1 |
| HB |  | 1.1 |  | 1.4 |
| $CO_x$'s |  | 7.4 |  | 6.1 |
| Yield (lb TMLA/lb PSC) |  | 1.56 |  | 1.56 |
| Acetic Acid Consumption (lb/lb TMLA) |  | 0.077 |  | 0.063 |

EXAMPLES IX-X

In order to further evaluate the high temperature separation process, synthetic slurry containing 1936 ppm of cobalt, 220 ppm of manganese, 4357 ppm of bromine, and 33% by weight of trimellitic acid was prepared. A heated bent sealed glass tube assembly was employed in test runs. The advantage of using a bent tube was that a high temperature separation could readily be performed in the sample.

Following the introduction of approximately 10g of slurry, solid oxalic acid dihydrate was added to the tube. The tubes were sealed with no precautions taken to exclude air. The tubes were then heated in an oil bath to the desired temperature and allowed to equilibrate for 15 minutes. Separation was performed quickly by tipping the tube outside of the oil bath. Care was taken to insure that the precipitated oxalate salts were not decanted with the mother liquor. Residual mother liquor was observed to remain with the precipitated salts. The tubes were then cut and the contents analyzed for catalyst metals and for percent solids using an absorbance technique.

Figure 1:
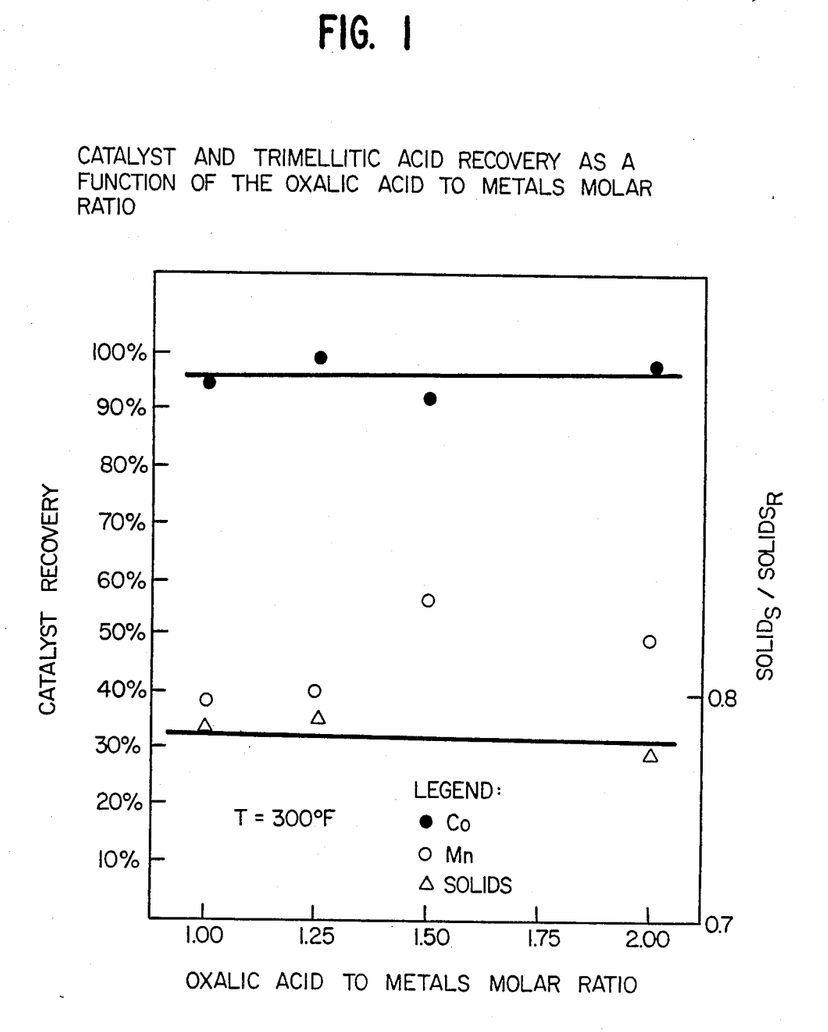
Figure 2:
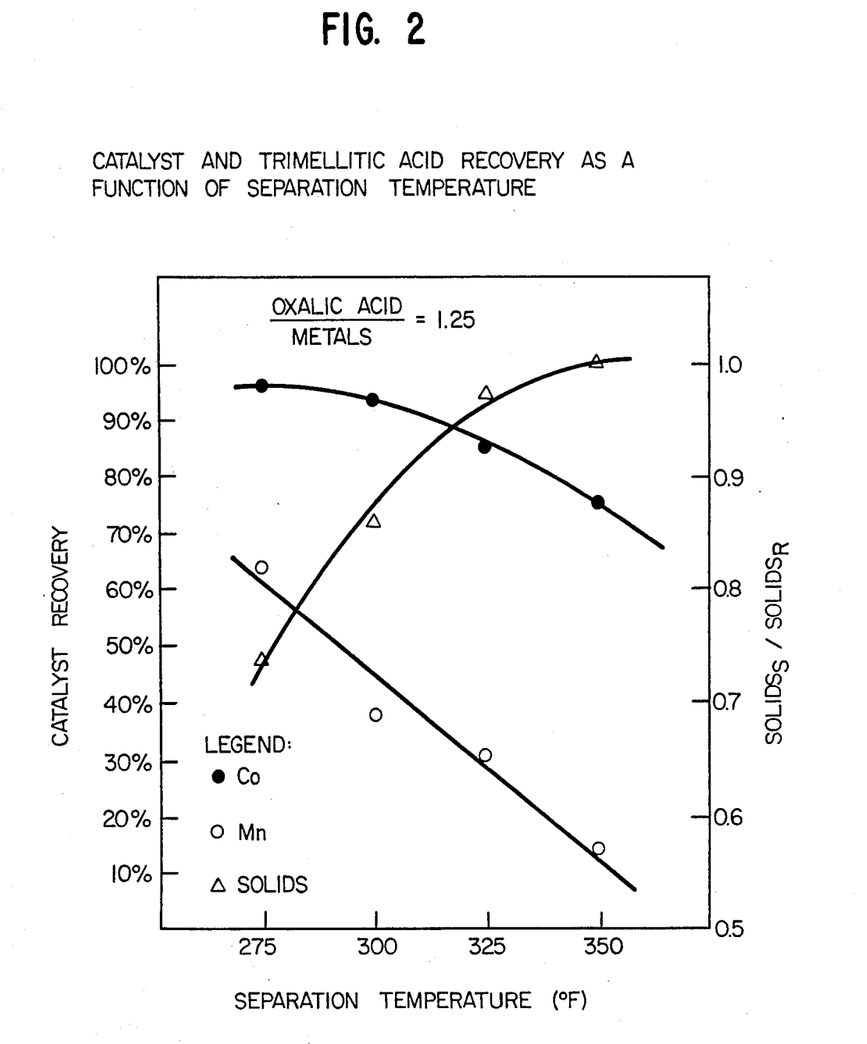

FIGS. 1 and 2 summarize the results of Examples IX and X, respectively. For these figures, the left-hand axis is the percentage of the catalyst metals recovered, after correction for residual mother liquor. The righthand axis is the ratio of solids (actually the percent total solids) in the mother liquor to solids in the oxalate residue. The solids in the residue includes both TMLA from residual mother liquor, as well as TMLA which was not soluble at the separation temperature. Since the metal, oxalate is not detected by the absorbance technique, this ratio would be 1 if all of the TMLA were soluble.

FIG. 1 illustrates the effect of the oxalic acid-to-metals mole ratio of the catalyst and TMLA recovery. As can be seen from this figure, cobalt recovery is relatively unaffected by changing the oxalic acid-to-metals ratio from 1.0 to 2.0. Manganese recovery did appear to increase at the higher oxalate ratios; however, the improvement in manganese recovery was relatively small—40 to 55%. As expected, the oxalic acid ratio did not appear to affect the separation of TMLA. Based on these results, there appears to be little incentive to use oxalic acid-to-metals ratio greater than 1; however, greater ratios can be employed. Since cobalt oxalate formation is favored over manganese, oxalate ratios less than 1 can be utilized without affecting the cobalt recovery.

FIG. 2 shows the effect of the separation temperature on both the catalyst and TMLA recovery. As expected, TMLA recovery increases with increasing separation temperature. Cobalt and manganese recovery both decrease, with the effect on manganese recovery being especially pronounced. Thermal decomposition of the oxalate salts, regenerating soluble catalyst metals species, is believed to be responsible for this effect. Based on these results, there appears to be a trade-off between catalyst and TMLA recovery. There may be an advantage to running the precipitation at a low temperature of about 250° F. to about 300° F., as this will maximize the catalyst metals recovery. TMLA that remains with the oxalate is recycled to the reactors. Alternatively, the solvent ratio is increased to increase TMLA solubility at the lower temperatures.

In addition to the above experiments, several tubes were prepared using material from a continuous run to test the effect of residence time at 300° F. and 1.25 oxalic acid ratio on the catalyst metals recovery. Samples were maintained at 300° F. for 20 and 75 minutes. While manganese recovery was observed to decrease at the higher residence time, the change was relatively small. Cobalt recovery was unchanged.

In all of our runs, both the sealed tube experiments and the pilot plant runs, cobalt recovery exceeded 90% while manganese recovery was generally in excess of 50%.

What is claimed is:

1. A continuous process for producing trimellitic acid by the continuous liquid-phase air oxidation of pseudocumene to trimellitic acid in a mother liquor comprising an acetic acid medium wherein weight ratio of pseudocumene to acetic acid is in the range of from about 1:1 to about 1:5, air oxygen partial pressure is in the range of from about 1 psi to about 20 psi in the presence of a cobalt-manganese-bromine catalyst wherein the mole ratio of cobalt-to-manganese is about 1.0:0.1 to about 1.0:5.0, the process comprising oxidation of pseudocumene in two stages comprising a first-stage oxidation at a temperature of about 250° F. to about 350° F. and a second-stage oxidation at a temperature of about 350° F. to about 450° F. wherein both air and the cobalt-manganese-bromine catalyst are added during both oxidation stages and recycling the cobalt-manganese metals of said catalyst by oxalate precipitation of metals of said catalyst at temperatures of about 250° F. to about 375° F. prior to the separation of said mother liquor from said trimellitic acid and using about 0.25 to about 2.5 moles of oxalic acid for the total moles of cobalt and manganese metals of said catalyst and continuously recycling the cobalt and manganese oxalates to the first-stage oxidation and mole ratio of bromine to total metals of the cobalt-manganese-bromine catalyst is from about 0.2:1.0 to about 2.0:1.0, bromine moles to total metals moles.

2. The process of claim 1 wherein said weight ratio of pseudocumene to acetic acid is in the range of from about 1:1.5 to about 1:3.

3. The process of claim 1 wherein said air oxygen partial pressure is in the range of from about 3.0 psi to about 10.0 psi.

4. The process of claim 1 wherein said mole ratio of cobalt to manganese is from about 1.0:0.2 to about 1.0:1.0.

5. The process of claim 1 wherein said mole ratio of bromine to total metals of the cobalt-manganese bromine catalyst is from about 0.5:1.0 to about 1.5:1.0, bromine moles to total metals moles.

6. The process of claim 1 wherein weight ratio of pseudocumene to acetic acid is in the range of from about 1:1.5 to about 1:3, air oxygen partial pressure is in the range of from about 3.0 to about 10.0 psi wherein the mole ratio of cobalt-to-manganese is about 1:0.2 to about 1:1, wherein mole ratios of said oxalic acid to said cobaltmanganese catalyst is about 0.5 to about 1.5:1, and mole ratio of bromine to total metals of the cobalt-manganesebromine catalyst is from about 0.5:1 to about 1.5:1, bromine moles to total metals moles.

7. A continuous process for producing trimellitic acid by the continuous liquid-phase air oxidation of pseudocumene to trimellitic acid in a mother liquor comprising an acetic acid medium wherein weight ratio of pseudocumene to acetic acid is in the range of from about 1:1 to about 1:5, air oxygen partial pressure is in the range of from about 1 to about 20 psi in the presence of a zirconium-cobalt-manganese-bromine catalyst wherein the mole ratio of cobalt-to-manganese is about 1.0:0.1 to about 1.0:5.0, and the mole ratio of zirconium-to-cobalt is about 0.005:1 to about 0.20:1.0, which process comprises conducting the oxidation of two stages comprising a first-stage reaction at a temperature of about 250° F. to about 350° F. and a second-stage oxidation at a temperature of about 350° about 450° F. wherein both air and the zirconium-cobalt-manganese-bromine catalyst are added during both oxidation stages and recycling the zirconium-cobalt-manganese metals of said catalyst by oxalate precipitation of metals of said catalyst at temperatures of about 250° F. to about 375° F. prior to the separation of said mother liquor from said trimellitic acid and using about 0.25 to about 2.5 moles of oxalic acid for the total moles of the zirconium, cobalt and manganese metals of said catalyst and continuously recycling the zirconium-cobalt-manganese oxalates to the first-stage oxidation and mole ratio of bromine to total metals of the zirconium-cobalt-manganese-bromine catalyst is from about 0.2:1.0 to about 2.0:1.0, bromine moles to total metal moles.

8. The process of claim 7 wherein said weight ratio of pseudocumene to acetic acid is in the range of from about 1:1.5 to about 1:3.

9. The process of claim 7 wherein said air oxygen partial pressure is in the range of from about 3.0 psi to about 10.0 psi.

10. The process of claim 7 wherein said mole ratio of zirconium-to-cobalt in said catalyst is from about 0.01:1.0 to about 0.10:1.0, and said mole ratio of said cobalt-to-manganese is from about 1.0:0.2 to about 1.0:1.0.

11. The process of claim 7 wherein said mole ratio of bromine to total metals of said zirconium-cobalt-manganese-bromine catalyst is from about 0.5:1 to about 1.5:1, bromine moles to total metal moles.

12. The process of claim 7 wherein weight ratio of pseudocumene to acetic acid is in the range of from about 1:1.5 to about 1:3, air oxygen partial pressure is in the range of from about 3.0 to about 10.0 psi wherein the mole ratio of zirconium-to-cobalt is about 0.01:1 to about 0.10:1, and said mole ratio of said cobalt-to-manganese is from about 1.0:0.2 to about 1.0:1.0 and wherein mole ratio of said oxalic acid to said zirconium-cobalt-manganese catalyst is about 0.5:1 to about 1.5:1, and mole ratio of bromine to total metals of the zirconium-cobalt-manganese-bromine catalyst is from about 0.5:1 to about 1.5:1, bromine moles to total metal moles.

* * * * *

UNITED STATES PATENT OFFICE
CERTIFICATE OF CORRECTION

Patent No. 4,816,601　　　　　　　　　　Dated March 28, 1989

Inventor(s) Lowry-Nowicki-Partenheimer

It is certified that error appears in the above-identified patent and that said Letters Patent is hereby corrected as shown below:

PATENT

| Column | Line | |
|---|---|---|
| 4 | 64 | "fe" should read --fed-- |
| 4 | 65 | "first-state" should read --first-stage" |
| 5 | 38 | "(HLA)," should read --(HMLA),-- |
| 6 | 5 | "secondstage" should read --second-stage-- |
| 6 | 45 | "irom" should read --from-- |
| 7 | 7 | "F.." should read --F.-- |
| 12 | 28 | "seccnd" should read --second-- |
| 13 | 66 | "righthand" should read --right-hand-- |
| 14 | 4 | "metal", should read --metal-- |
| 14 | 46-47 | "smal-1--40" should read --small--40-- |
| 16 | 1 | "cobaltmanganese" should read --cobalt-manganese-- |
| 16 | 2-3 | "cobalt-manganesebromine" should read --cobalt-manganese-bromi: |
| 16 | 19 | -"about" should read --to about-- |

Signed and Sealed this

Twenty-first Day of November, 198!

Attest:

JEFFREY M. SAMUELS

Attesting Officer　　　　Acting Commissioner of Patents and Trademarks